US008955237B2

(12) United States Patent
Rini et al.

(10) Patent No.: US 8,955,237 B2
(45) Date of Patent: Feb. 17, 2015

(54) DETACHABLE POST-OPERATIVE PROTECTIVE DEVICE FOR THE TOES AND FOREFOOT

(76) Inventors: David A. Rini, Monkton, MD (US); Brent G. Parks, West Friendship, MD (US); Christopher P. Chiodo, Walpole, MA (US); Lew C. Schon, Baltimore, MD (US)

( * ) Notice: Subject to any disclaimer, the term of this patent is extended or adjusted under 35 U.S.C. 154(b) by 1252 days.

(21) Appl. No.: 11/612,204

(22) Filed: Dec. 18, 2006

(65) Prior Publication Data

US 2008/0141565 A1    Jun. 19, 2008

(51) Int. Cl.
*A43C 13/14* (2006.01)
*A61F 5/01* (2006.01)
*A43B 23/08* (2006.01)
*A43B 7/00* (2006.01)

(52) U.S. Cl.
CPC ............... *A43B 23/087* (2013.01); *A43B 7/00* (2013.01); *A61F 5/0195* (2013.01)
USPC ............................... 36/110; 36/72 R; 602/11

(58) Field of Classification Search
CPC ........ A43B 7/00; A43C 13/14; A61F 5/0195; A61F 13/041; A61F 13/043; A61F 15/008
USPC .......... 36/72 R, 77 R, 77 M, 96, 110; 602/11, 602/30; 128/893
See application file for complete search history.

(56) References Cited

U.S. PATENT DOCUMENTS

| | | | |
|---|---|---|---|
| 2,292,297 A | 8/1942 | Sherlock | |
| 3,040,455 A | 7/1961 | Criswell | |
| 3,263,679 A | 8/1966 | Hass | |
| 3,661,151 A | 5/1972 | Schoenbrun et al. | |
| 3,716,932 A | 2/1973 | Pakulak | |
| 3,773,041 A * | 11/1973 | Bogar et al. | 602/10 |
| 4,061,138 A | 12/1977 | Bernstein | |
| 4,177,583 A | 12/1979 | Chapman | |
| 4,333,248 A | 6/1982 | Samuels | |
| 4,566,208 A | 1/1986 | Shaffner | |
| 5,185,945 A * | 2/1993 | Nielsen et al. | 36/77 R |
| 5,342,070 A * | 8/1994 | Miller et al. | 280/11.231 |
| 5,452,527 A * | 9/1995 | Gaylord, Jr. | 36/110 |
| 5,778,565 A | 7/1998 | Holt et al. | |
| 5,832,560 A * | 11/1998 | DePalma | 16/30 |
| 6,029,373 A * | 2/2000 | Diradour et al. | 36/12 |
| 6,056,712 A * | 5/2000 | Grim | 602/27 |
| 6,272,771 B1 | 8/2001 | Rodi | |
| 6,305,101 B2 * | 10/2001 | Chemello | 36/10 |

(Continued)

*Primary Examiner* — Khoa Huynh
*Assistant Examiner* — Sharon M Prange
(74) *Attorney, Agent, or Firm* — Sughrue Mion, PLLC

(57) ABSTRACT

A protective member having a substantially flat base portion, and a substantially cup-shaped member extending from a forward end of the base portion. The base portion is attachable to a shoe, such that the cup-shaped member substantially encapsulates and protects a forefoot and toe region. Further, at least one opening is provided in a forward portion of the cup-shaped member to allow access to the forefoot and toe region. The cup-shaped member is further defined by an anterior portion extending upward from the base portion, a dorsal extension portion extending from an upper end of the anterior portion, where the dorsal extension portion provided to substantially cover a top portion of the forefoot and toe region, and at least one lateral extension portion extending from a side end of the anterior portion, where the at least one lateral extension portion provided to substantially cover a lateral portion of said forefoot and toe region.

22 Claims, 3 Drawing Sheets

(56) References Cited

U.S. PATENT DOCUMENTS

| | | | |
|---|---|---|---|
| 6,389,715 B1 * | 5/2002 | Krajcir | 36/77 R |
| 6,505,422 B2 * | 1/2003 | Racine | 36/115 |
| 6,836,980 B2 | 1/2005 | Woods | |
| 7,062,868 B2 | 6/2006 | Frulla | |

* cited by examiner

DETACHABLE POST-OPERATIVE PROTECTIVE DEVICE FOR THE TOES AND FOREFOOT

BACKGROUND OF THE INVENTION

The present invention generally relates to a protective device for the toes and forefoot, the protective device being detachable from a shoe or other suitable footgear.

Following orthopedic surgery or injury of the forefoot, a patient may be required to wear a type of orthopedic shoe to protect the toes and forefoot. For example, after a bunionectomy or hammer-toe correction surgery, fixation pins are left protruding from the patient's toes during the healing process. Therefore, the wound area must be protected from further injury or infection. In related protective members, the entire toe area is covered or encased. Such members, however, do not allow for easy visual inspection or access to the wound area without prior removal of the protective member.

SUMMARY OF THE INVENTION

In view of the foregoing, aspects of the present invention are provided to allow for easy visual inspection of a wound area without removal of the protective member, while at the same time protecting the wound area and preventing clothing, bed linens, etc., from being snagged on the wound area.

In an illustrative, non-limiting embodiment, a protective member is provided. The protective member has a substantially flat base portion, and a substantially cup-shaped member extending from a forward end of the base portion. The base portion is attachable to a shoe, such that the cup-shaped member substantially encapsulates and protects a forefoot and toe region. Further, at least one opening is provided in a forward portion of the cup-shaped member to allow access to the forefoot and toe region. The cup-shaped member is further defined by an anterior portion extending upward from the base portion, a dorsal extension portion extending from an upper end of the anterior portion, where the dorsal extension portion provided to substantially cover a top portion of the forefoot and toe region, and at least one lateral extension portion extending from a side end of the anterior portion, where the at least one lateral extension portion provided to substantially cover a lateral portion of said forefoot and toe region.

BRIEF DESCRIPTION OF THE DRAWINGS

Aspects of illustrative, non-limiting embodiments of the present invention will become more apparent by describing in detail embodiments thereof with reference to the attached drawings in which.

DETAILED DESCRIPTION OF THE INVENTION

The following description of illustrative, non-limiting embodiments of the invention discloses specific configurations and components. However, the embodiments are merely examples of the present invention, and thus, the specific features described below are merely used to more easily describe such embodiments and to provide an overall understanding of the present invention. Accordingly, one skilled in the art will readily recognize that the present invention is not limited to the specific embodiments described below. Furthermore, the descriptions of various configurations and components of the present invention that are known to one skilled in the art are omitted for the sake of clarity and brevity.

Figure 1:
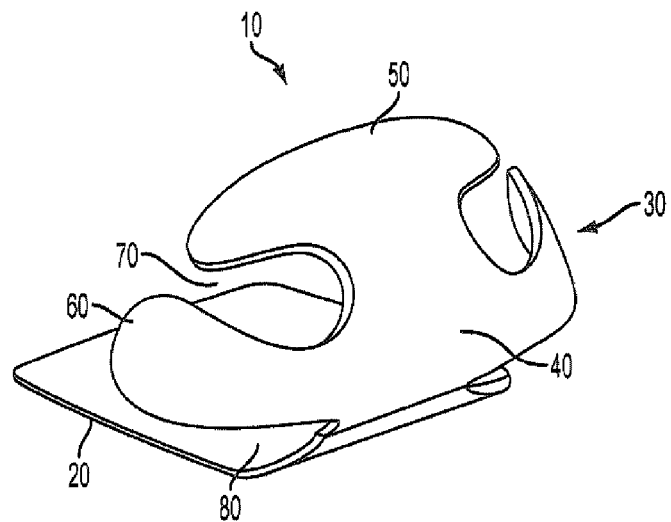
FIG. 1 shows a perspective view of a protective member.

FIG. 1 shows a protective device for the toes and forefoot according to an illustrative, non-limiting embodiment of the present invention. As shown, a protective member 10 has a substantially flat base portion 20 and a semi-rigid, substantially cup-shaped member 30 extending from a forward end of the base portion 20. The cup-shaped member 30 is provided with an anterior portion 40 extending upward from the base portion 20, a dorsal extension portion 50 extending from an upper end of the anterior portion 40, lateral extension portions 60 extending from a side end of the anterior portion 40, a space 70 provided between the dorsal extension portion 50 and the lateral extension portions 60 and a space 80 provided between the lateral extension portions 60 and the base portion 20. As shown in FIG. 1, a lower end of the anterior portion 40 is connected to the base portion 20. This lower end of the anterior portion 40 has a width narrower than a width of the base portion in a fully assembled state.

The protective member 10 should be strong enough to withstand impact with objects, etc, but preferably bendable such that the anterior portion 40 and lateral extension portions 60 can be bent inwardly or outwardly to accommodate varying size forefeet (i.e., semi-rigid). The protective member 10 may be injection molded (low cost) and may be made of polypropylene or other suitable materials such as nylon or other plastics. The entire protective member 10, or just merely the base portion 20 of the protective member 10, can alternatively be made of metal.

Figure 2:
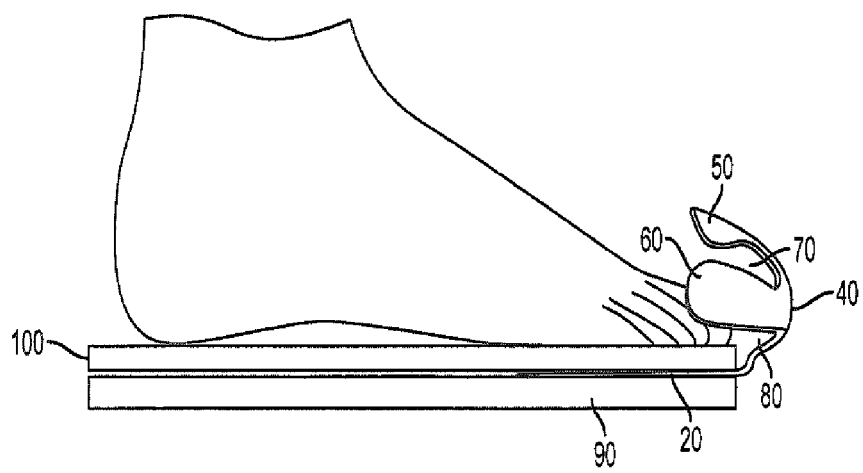
FIG. 2 shows a side view of the protective member in regard to placement of a patient's foot.

As shown in the non-limiting embodiment of FIG. 2, the cup-shaped member 30 defines a receiving area for housing and protecting a forefoot and toes. Further, the spaces 70, 80 allow for visual inspection of the forefoot and toes when they are housed in the cup-shaped member 30 without the need of removing the protective member 10. Accordingly, the patient, family and healthcare providers are provided with easy access to the wound area for proper monitoring of concerns such as infection, swelling, poor blood flow or other important clinical signs. As further shown in FIG. 2, the protective member 10 is preferably held between a sole 90 and insole 100 of a post-operative shoe (not shown). Specifically, the forward end of the base plate of the protective member 10 is aligned with a forward end of the insole 100. Since the anterior portion 40 of the protective member 10 is curved outward in a forward direction from the base portion 20, sufficient clearance is provided for fixation pins that may be left protruding from the patient's toes following surgery. Similarly, since the dorsal extension portion 50 and the lateral extension portions 60 curve around and over the forefoot and toes, sufficient clearance is provided for fixation pins, swelling, etc., due to surgery, while at the same time, providing protection from falling objects, clothing, contact with objects such as furniture, etc. The spacing or clearance provided by the protective device can also accommodate post-operative padding, dressings, gauze and support material as needed.

As further shown in FIG. 2, the base portion 20 preferably extends to just behind the metatarsal head or plantar of the foot (i.e., the portion of the foot that contacts the insole 100). However, the base portion can alternatively be formed to extend the entire length of the foot or insole 100.

Figure 3A:
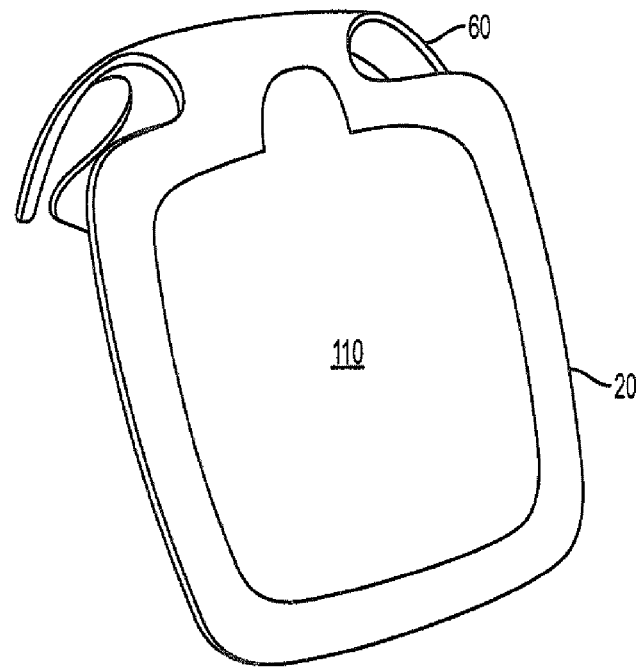
FIG. 3A shows a bottom view of the protective member with adhesive strip.
Figure 3B:
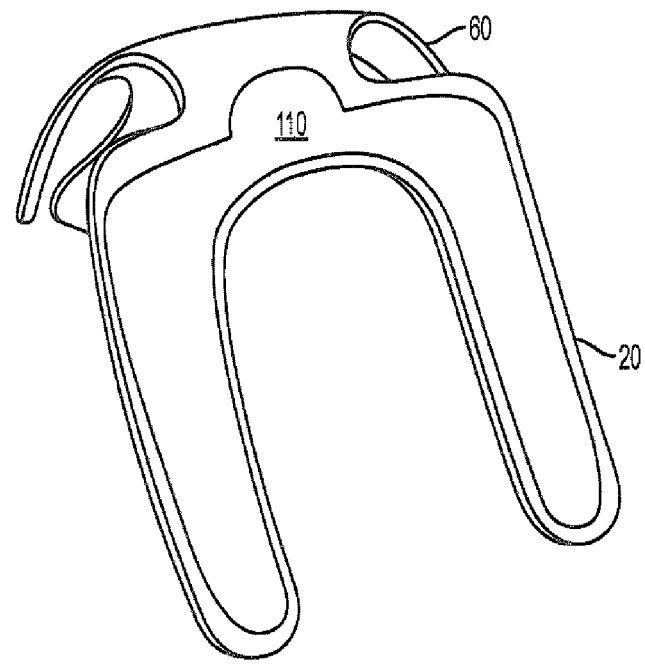
FIG. 3B shows a bottom view of the protective member in a horseshoe shape variant of the base portion.

As shown in the non-limiting embodiment of FIG. 3A, the base portion 20 is substantially rectangular shaped, but can be formed of any other suitable shape. For example, the non-limiting embodiment of FIG. 3B shows the base portion 20 formed as a horseshoe shape. The opening provided by the horseshoe variant helps to reduce pressure or stress on the forefoot of the patient while standing or walking. Also, as shown in FIGS. 3A and 3B, a mounting portion 110 in the form of an adhesive member may be provided on the bottom surface of the base portion 20. The adhesive member (110) can be formed of a double-sided adhesive having a release paper attached thereto. As shown in FIG. 2, the adhesive member (110) is attached to a sole 90 of a post-operative shoe (not shown). An adhesive member can also be provided on a top surface of the base portion 20 if needed. The adhesive member (110) allows the protective member 10 to be readily attached and detached from the shoe sole 90. Alternatively, different types of mounting portions 110 may be provided such as VELCRO®, snaps, connection tabs, etc.

Also, as viewable in FIGS. 3A and 3B, the lateral extension portions 60 form a substantially square shape that follows the contour of an insole 100 to which the protective member 10 is attached. This allows the protective member 10 to be used for either a right or left foot. The lateral extension portions 60 can alternatively form a more circular shape around the forefoot.

Figure 4A:
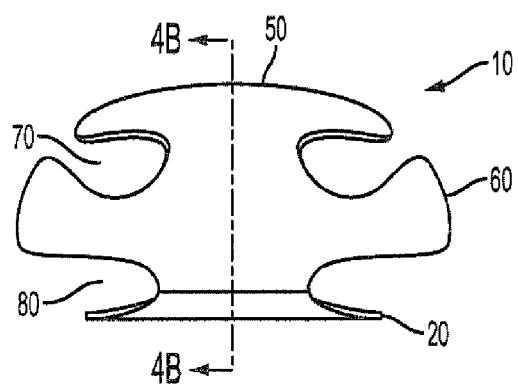
FIG. 4A shows a front view of the protective member.
Figure 4B:
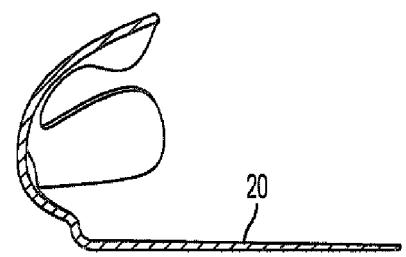
FIG. 4B shows a cross-section of line A-A of FIG. 4A.

A front view of the protective member 10 is shown in FIG. 4A. The space 80 provided between the lateral extension portions 60 and the base portion 20 is more clearly seen in this view. A cross-section, taken along line A-A of FIG. 4A is shown in FIG. 4B. As shown in FIG. 4B, the base portion 20 may be tapered from a forward end to a rear end. Such tapering reduces a ridge between the base portion 20 and the insole 100 and helps to alleviate the stress or pressure that the base portion 20 exerts on the forefoot. As merely exemplary, the base portion 20 is shown to taper from 3 mm to 1.5 mm.

The previous description of the non-limiting embodiments is provided to enable one skilled in the art to make and use the present invention. Moreover, various modifications to these embodiments will be readily apparent to those skilled in the art, and the generic principles and specific examples defined herein may be applied to other embodiments without the use of inventive faculty. Therefore, the present invention is not intended to be limited to the embodiments described herein, but is to be accorded the widest possible scope as defined by the recitations of the claims and equivalents thereof.

What is claimed is:

1. A protective member comprising:
a substantially flat base portion;
a receiving member, being cup-shaped, extending from a forward end of said base portion, wherein said base portion is attachable to a shoe, such that said receiving member substantially protects a forefoot and toe region,
wherein at least two openings are provided on the receiving member, a first opening being provided in a forward, upper portion of said receiving member, and a second opening provided in a forward, lower portion of said receiving member, the at least two opening remaining open when the protective member is in a fully assembled state so as to allow access to said forefoot and toe region,
wherein said receiving member comprises:
an anterior portion that extends upward, substantially perpendicular to said base portion, at a position that is forward of said forefoot and toe region and said forward end of said base portion so as not to cover said forefoot and toe region and said forward end of said base portion,
at least one lateral extension portion extending from a side end of said anterior portion, so as to extend from said position forward of said forefoot and toe region and said forward end of said base portion to a position that substantially covers a lateral portion of said forefoot and toe region, and
a dorsal extension portion extending from an upper end of said anterior portion, so as to extend from said position forward of said forefoot and toe region and said forward end of said base portion to a position that substantially covers a top portion of said forefoot and toe region,
wherein the first opening is defined by a space provided between said dorsal extension portion and said at least one lateral extension portion and, and the second opening is provided between said at least one lateral extension portion and said base portion, and
wherein said at least one lateral extension portion has a curvature which has a curved shape along a length of the lateral extension portion and extends outwardly in a lateral direction to curve outward in the lateral direction relative to said base portion, the curvature of the lateral extension portion extending more outwardly in a lateral direction than the base portion such that a side clearance is formed between said forefoot and toe region and an inner surface of said at least one lateral extension portion,
wherein the receiving member and the base portion are connected at a lower end of the anterior portion, said lower end having a width which is narrower than a width of the base portion in a fully assembled state.

2. The protective member according to claim 1, wherein a forward clearance is provided between said forefoot and toe region and an inner surface of said anterior portion.

3. The protective member according to claim 1, wherein two lateral extension portions are provided, such that one lateral extension portion extends from a left side of said anterior portion and a second lateral extension portion extends from a right side of said anterior portion.

4. The protective member according to claim 1, wherein said receiving member is bendable.

5. The protective member according to claim 1, wherein a top clearance is provided between said forefoot and toe region and an inner surface of said dorsal extension portion.

6. The protective member according to claim 1, wherein said base portion is substantially rectangular shaped.

7. The protective member according to claim 1, wherein said base portion is substantially horseshoe shaped.

8. The protective member according to claim 1, wherein said base portion is tapered, in cross-section, from said forward end to a rear end.

9. The protective member according to claim 1, wherein said receiving member is formed of a semi-rigid material.

10. A protective shoe comprising:
a sole;
an insole disposed on top of said sole; and
a protective member;
said protective member comprising:
a substantially flat base portion held between said sole and insole and attached to a forward end of said sole;
a receiving member, being cup-shaped, provided at a forward end of said base portion, such that said receiving member substantially protects a forefoot and toe region, and
wherein at least two openings, are provided on the receiving member a first opening being provided in a forward, upper portion of said receiving member and a second opening being provided in a forward, lower portion of said receiving member, the at least two openings remaining open when the protective member is in a fully assembled state so as to allow access to said forefoot and toe region, wherein said receiving member comprises:

an anterior portion that extends upward, substantially perpendicular to said base portion, at a position that is forward of said forefoot and toe region and said forward end of said base portion so as not to cover said forefoot and toe region and said forward end of said base portion, and at least one lateral extension portion extending from a side end of said anterior portion, so as to extend from said position forward of said forefoot and toe region and said forward end of said base portion to a position that substantially covers a lateral portion of said forefoot and toe region, wherein the receiving member and the base portion are connected at a lower end of the anterior portion, said lower end having a width which is narrower than a width of the base portion in a fully assembled state, wherein said at least one lateral extension portion has a curvature having a curved shape along a length of the lateral extension portion and extends outward in a lateral direction relative to said base portion, the curvature of the lateral extension portion extending more outwardly in a lateral direction than the base portion such that a side clearance is formed between said forefoot and toe region and an inner surface of said at least one lateral extension portion.

11. The protective shoe according to claim 10, wherein said receiving member further comprises:

a dorsal extension portion extending from an upper end of said anterior portion, so as to extend from said position forward of said forefoot and toe region and said forward end of said base portion to a position that substantially covers a top portion of said forefoot and toe region.

12. The protective shoe according to claim 11, wherein the first opening is defined by a space provided between said dorsal extension portion and said at least one lateral extension portion and, the second opening is provided between said at least one lateral extension portion and said base portion.

13. The protective member according to claim 11, wherein a forward clearance is provided between said forefoot and toe region and an inner surface of said anterior portion.

14. The protective member according to claim 11, wherein two lateral extension portions are provided, such that one lateral extension portion extends from a left side of said anterior portion and a second lateral extension portion extends from a right side of said anterior portion.

15. The protective member according to claim 11, wherein a top clearance is provided between said forefoot and toe region and an inner surface of said dorsal extension portion.

16. The protective member according to claim 10, wherein said base portion is attached to said sole via a mounting portion.

17. The protective member according to claim 16, wherein said mounting portion comprises an adhesive member.

18. The protective member according to claim 10, wherein said base portion extends to a metatarsal head of a foot.

19. The protective member according to claim 10, wherein said receiving member is bendable.

20. The protective member according to claim 10, wherein said base portion is substantially rectangular shaped.

21. The protective member according to claim 10, wherein said base portion is substantially horseshoe shaped.

22. The protective member according to claim 10, wherein said base portion is tapered, in cross-section, from said forward end to a rear end.

\* \* \* \* \*